(12) United States Patent
Haase et al.

(10) Patent No.: US 12,023,189 B2
(45) Date of Patent: Jul. 2, 2024

(54) BLOOD FLOW MEASUREMENT BASED ON VESSEL-MAP SLOPE

(71) Applicant: KONINKLIJKE PHILIPS N.V., Eindhoven (NL)

(72) Inventors: Christian Haase, Hamburg (DE); Michael Grass, Buchholz in der Nordheide (DE); Romane Isabelle Marie-Bernard Gauriau, Paris (FR); Martijn Anne Van Lavieren, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 601 days.

(21) Appl. No.: 17/263,469

(22) PCT Filed: Aug. 2, 2019

(86) PCT No.: PCT/EP2019/070854
§ 371 (c)(1),
(2) Date: Jan. 26, 2021

(87) PCT Pub. No.: WO2020/025780
PCT Pub. Date: Feb. 6, 2020

(65) Prior Publication Data
US 2021/0161495 A1    Jun. 3, 2021

(30) Foreign Application Priority Data
Aug. 3, 2018 (EP) .................................... 18290092

(51) Int. Cl.
*A61B 6/50* (2024.01)
*A61B 6/00* (2024.01)
(Continued)

(52) U.S. Cl.
CPC .............. *A61B 6/504* (2013.01); *A61B 6/481* (2013.01); *G06T 7/0012* (2013.01); *G16H 50/20* (2018.01);
(Continued)

(58) Field of Classification Search
CPC ....... A61B 6/504; A61B 6/481; A61B 8/5223; A61B 5/02007; A61B 6/5205;
(Continued)

(56) References Cited

U.S. PATENT DOCUMENTS

| 9,072,490 B2 | 7/2015 | Sakaguchi et al. |
| 10,052,036 B2 | 8/2018 | Lading et al. |

(Continued)

FOREIGN PATENT DOCUMENTS

| CN | 101005803 A | * | 7/2007 | ............ A61B 6/032 |
| JP | 2012520102 A | * | 9/2012 | |

(Continued)

OTHER PUBLICATIONS

Machine translation of JP2012520102A (Year: 2012).*
(Continued)

*Primary Examiner* — John Villecco
*Assistant Examiner* — Courtney Joan Nelson

(57) ABSTRACT

An apparatus for assessing a coronary vasculature and a corresponding method are provided which allow to globally assess a coronary artery disease directly from the contrast agent dynamics as derived from diagnostic images acquired using an invasive medical imaging modality by following the time course of the area occupied by the vessels in the diagnostic images.

20 Claims, 4 Drawing Sheets

(51) Int. Cl.
*G06T 7/00* (2017.01)
*G16H 50/20* (2018.01)

(52) U.S. Cl.
CPC .............. *G06T 2207/20081* (2013.01); *G06T 2207/30104* (2013.01)

(58) Field of Classification Search
CPC ..... A61B 6/5217; A61B 8/0891; A61B 5/004; A61B 6/463; A61B 8/0883; A61B 5/026; A61B 5/0275; A61B 5/489; A61B 5/72; A61B 2576/00; A61B 6/507; A61B 6/503; A61B 2576/023; A61B 5/0035; A61B 5/0044; A61B 5/02; A61B 5/02028; A61B 5/021; A61B 5/024; A61B 5/029; A61B 5/145; A61B 5/4884; A61B 8/02; A61B 8/04; A61B 8/06; A61B 8/065; A61B 8/481; A61B 8/5261; G06T 7/0012; G06T 2207/30104; G06T 2207/30048; G06T 2210/41; G06T 2211/404; G06T 2207/20081; G16H 30/40; G16H 50/50; G16H 50/20
See application file for complete search history.

(56) References Cited

U.S. PATENT DOCUMENTS

| | | | |
|---|---|---|---|
| 11,324,410 | B2 | 5/2022 | Burkett |
| 11,382,569 | B2 | 7/2022 | Grady et al. |
| 2013/0116739 | A1 | 5/2013 | Brada |
| 2014/0276140 | A1* | 9/2014 | Kinghorn .............. A61B 5/366 600/521 |
| 2015/0051888 | A1 | 2/2015 | Itu |
| 2015/0313478 | A1* | 11/2015 | Veszelei ............. A61B 5/02158 600/483 |
| 2015/0327780 | A1* | 11/2015 | Kano ................... A61B 90/37 600/407 |
| 2016/0066800 | A1 | 3/2016 | Sharma |
| 2016/0073970 | A1 | 3/2016 | Sharma |

FOREIGN PATENT DOCUMENTS

| | | | |
|---|---|---|---|
| WO | WO2000053081 | A1 * | 9/2000 |
| WO | 2006061814 | A1 | 6/2006 |
| WO | 2015138555 | A2 | 9/2015 |

OTHER PUBLICATIONS

"Coronary CT Angiography-derived Fractional Flow Reserve;" Christian Tesche, Carlo N. De Cecco, Moritz H. Albrecht, Taylor M. Duguay, Richard R. Bayer II, Sheldon E. Litwin, Daniel H. Steinberg, and U. Joseph Schoepf Radiology 2017 285:1, 17-33 (Year: 2017).*
Machine translation of CN-101005803-A from Search (Year: 2007).*
International Search Report and Written Opinion of PCT/EP2019/070854, dated Nov. 20, 2019.
Tesche, Christian et al."Coronary CT Angiography-derived Fractional Flow Reserve", Radiology, vol. 285, No. 1, Oct. 2017, pp. 17-33.

* cited by examiner

BLOOD FLOW MEASUREMENT BASED ON VESSEL-MAP SLOPE

CROSS-REFERENCE TO PRIOR APPLICATIONS

This application is the U.S. National Phase application under 35 U.S.C. § 371 of International Application No. PCT/EP2019/070854, filed on Aug. 2, 2019, which claims the benefit of European Patent Application No. 18290092.8, filed on Aug. 3, 2018. These applications are hereby incorporated by reference herein.

FIELD OF THE INVENTION

The present invention relates to an apparatus for assessing a coronary vasculature, a corresponding method and a respective computer program. In particular, the present invention relates to an apparatus for globally assessing coronary artery disease by enabling a direct determination of flow-related hemodynamic parameters using contrast agent dynamics as tracked via two time-series of diagnostic images.

BACKGROUND OF THE INVENTION

Coronary blood flow measurements are an important tool for the assessment of coronary artery disease, as they allow to improve the understanding of the coronary lesions. More particularly, these measurements allow to determine consequences of coronary artery disease, such as the ischemic potential, and also provide treatment guidance for a patient. For this purpose, coronary blood flow measurements are typically performed under resting conditions and under hyperemic conditions in order to determine flow-related properties, such as flow velocity or volumetric flow rate for both states.

Based on these measurements, various flow-related indices can be determined. One important index is the so-called Coronary Flow Reserve (CFR), which defines the maximum increase in blood flow through the vasculature above the normal resting volume. The CFR may be calculated from the ratio between the hyperemic flow velocity $v_H$ and the resting flow velocity $v_R$.

Despite the well-known benefits of these measurements, routine flow measurements have not found their way into clinical practice, due to the added complexity and the lack of robustness of any measurement techniques available for measuring flow-related parameters.

US 2013/0116739 A1 discloses a method and apparatus for detecting and analyzing heart mechanical activity at a region of interest of a patient's heart. The method comprises acquiring a time sequence of 2-dimensional X-ray images of a region of interest over at least part of a cardiac cycle, detecting coronary vessels in the X-ray images, tracking the coronary vessels through the sequence of images to identify movements of the coronary vessels; and analyzing the movements of the coronary vessels to quantify at least one parameter characterizing heart wall motion in the region of interest.

US 2015/0327780 A1 discloses an image processing apparatus including a processing circuitry that is configured to obtain images in a time series including images of a blood vessel of a subject and correlation information indicating a correlational relationship between physical indices of the blood vessel and function indices of the blood vessel related to vascular hemodynamics, calculate blood vessel morphology indices in a time series indicating morphology of the blood vessel of the subject, on a basis of the images in the time series, and identify a function index of the blood vessel of the subject, by using a physical index of the blood vessel of the subject obtained from the blood vessel morphology indices, on a basis of the correlation information.

SUMMARY OF THE INVENTION

Thus, approaches have been made to avoid having to measure these flow-related properties directly at resting and hyperemic conditions and instead allow to derive these properties from measurements other than flow measurements.

One particular approach is to derive the flow-related property values, such as the flow velocity values, directly from the contrast agent dynamics in consecutive frames of an angiography series. An example of such an approach is the so-called TIMI frame count (TFC). In TFC, the number of frames of image data required for a contrast agent to reach a standardized distal coronary landmark in a vessel are counted and used to derive flow velocity. However, approaches based on contrast agent dynamics are typically time consuming, complex and affected by foreshortening of the used artery segment. Further, these approaches generally allow the assessment of the flow related properties in a global manner, i.e. for the entire coronary artery tree (or portions thereof).

One possible way to determine the flow-related properties for a particular patient in a more site-specific manner is to approximate these properties using a geometric model of the coronary artery, or vessel, and computing the corresponding flow-related properties using a fluid dynamics model which models the blood flow through the vessel modeled in the geometric model. However, to be accurate, these approaches require an appropriate determination of boundary conditions and, thus, require sufficient expertise and experience.

It is therefore an object of the invention to provide a system and method which allows for a more accurate and straightforward determination of flow-related properties. It is a further object of the invention to provide a system and method which enables to provide a global assessment of flow-related indices, such as CFR, in a direct and time-efficient manner. It is an even further object of the invention to provide a system and method enabling to provide a local assessment of flow-related indices in a straightforward and robust manner. More particularly, it is an object of the invention to provide a system and a method that allows for assessment of flow-related properties, such as blood flow velocity, volumetric flow rate or the like, and, accordingly, of flow-related indices, such as CFR, without the need of a fluid dynamics model.

This object is achieved by an apparatus for assessing a coronary vasculature comprising an input unit configured to receive a first time series of diagnostic images of a plurality of vessels in the coronary vasculature, and a second time series of diagnostic images of the plurality of vessels in the coronary vasculature, the first time series and the second time series having been acquired with different acquisition conditions, whereby each one of the diagnostic images of the first time series and each one of the diagnostic images of the second time series respectively represents a visualization of a contrast agent dynamics for a particular point in time, a computation unit configured to compute, for the first time series of diagnostic images, a first time series of vessel map feature values of a first dynamic vessel map representing the plurality of vessels, and compute, for the second time series of diagnostic images, a second time series of vessel map feature values of a second dynamic vessel map representing the plurality of vessels, the first time series of vessel map feature values and the second time series of vessel map feature values being indicative of the contrast agent evolution over time, and an analyzation unit configured to compare the first time series of vessel map feature values and the second time series of vessel map feature values and to derive, based on the comparing, at least one global hemodynamic parameter.

In this context, the term time series refers to a plurality of diagnostic images that have been acquired over time. More particularly, these time series may comprise a plurality of diagnostic images with which the contrast agent dynamics through a vasculature can be visualized and, by means of this visualization, the contrast agent dynamics can be tracked. The diagnostic images may hereby be acquired by any medical imaging modality capable of visualizing contrast agent in the vasculature. One particular imaging method which allows to acquire the diagnostic images is X-ray imaging.

Each one of the diagnostic images of the first time series and the second time series hereby represents the visualization of the contrast agent dynamics for a particular point in time. To this end, the term point in time shall be understood as referring to a certain point in measurement time relative to the moment of injection of the contrast agent. In other words, for each measurement, the time is measured starting at the moment at which the contrast agent is injected. Accordingly, the acquisition of the diagnostic images starts upon injection of the contrast agent. Hereby, the first diagnostic images of a particular time series only visualize a small part of the vasculature as the contrast agent has not yet reached and/or completely filled any of the vessels. Over time, the contrast agent reaches more and more vessels. Thus, the amount of vessels visible in the diagnostic images grows over time and represents a vessel map.

To this end, it shall be understood that the term vessel map is to be interpreted broadly and may also refer to single vessels being visible in the diagnostic images at the beginning of the injection. Over time, the contrast agent flows into more and more vessels and the vessel map occupies more and more area in the diagnostic images. Given that the contrast agent dynamic is affected by the same narrowings and friction as the blood flow, the time-evolution of the vessel map during contrast agent inflow provides an indication about the hemodynamics inside the vasculature.

The term vessel map feature thus refers to a particular feature of the vessel map as visualized in the diagnostic images. In some embodiments, this feature of the vessel map may particularly be an area occupied by the vessels in the diagnostic images. In some embodiments the feature of the vessel map may also be the quantity of the vessels visible in the pictures. Other vessel map features may also be envisioned as long as they allow to track the contrast agent evolution through the vasculature over time.

The term time series of vessel map feature values hereby refers to a plurality of vessel map feature values as derived from the vessel maps visualized in the corresponding plurality of diagnostic images of the time series of diagnostic images. In other words, for each diagnostic image in the time series, acquired at a particular point in measurement time, a vessel map feature value is derived and, thus, corresponds to that particular point in measurement time.

The thus derived first time series of vessel map features and the second time series of vessel map features are compared to another and, based on the comparison, a global hemodynamic parameter is derived. In this context, the term global means that the hemodynamic parameter is not specified for one particular vessel or vessel location, i.e. is not a parameter that would locally occur at that position, but is a hemodynamic parameter representing the vasculature as a whole.

To this end, the term vasculature may particularly refer to a plurality of vessels of one vessel tree. In some embodiments, the term vasculature may also refer to sub-branches, such as the LAD or LCX) of one vessel tree. The term hemodynamic parameter may refer to any kind of parameter indicative of the blood flow properties inside the vessels. In some embodiments, the hemodynamic parameter may particularly be a flow-related hemodynamic parameter. In some embodiments, the hemodynamic parameter may be the coronary flow reserve.

The first and second time series have been acquired under different respective conditions. As an example, the first time series may be acquired under resting conditions of a patient and the second time series may be acquired under hyperemic conditions. Alternatively or additionally, the different states could also refer to a time series acquired during contrast agent inflow and the other time series under contrast agent outflow, whereby the measurement time for the first time series is measured in relation to the time point of injection of the contrast agent and the measurement time for the second time series is measured in relation to the time point of starting of the outflow of the contrast agent. The apparatus therefore enables a global assessment of the coronary vasculature by means of a global hemodynamic parameter, whereby the global hemodynamic parameter may be directly derived from imaging data without the need of segmentation of the diagnostic images and the identification of individual vessels.

In some embodiments, the first time series of diagnostic images and the second time series of diagnostic images is obtained using X-ray angiography.

As indicated, any medical imaging modality capable of visualizing contrast agent may be used to monitor the contrast agent dynamics through the vasculature of interest. In some particular embodiments X-ray angiography, in particular invasive X-ray angiography, is used to obtain the first and second time series of diagnostic images. Hereby, the diagnostic images of the first time series and the second time series, respectively, should be collected from the same projection direction, such as to obtain comparable diagnostic images for both conditions. The acquisition of the first and second time series using invasive X-ray angiography encompasses insertion of a contrast agent injection catheter and injection of the contrast agent into the vasculature. Upon injection, X-ray image acquisition is started, so that a plurality of X-ray angiography images are collected at predefined intervals. In some embodiments, the acquisition of these images is performed every 10 to 200 ms, more specifically every 20 to 100 ms, even more specifically every 50 ms. This achieves rates of 15 to 30 images per second.

In some embodiments, the first dynamic vessel map represents the inflow of a contrast agent into the plurality of vessels as a function of time under resting conditions and the second dynamic vessel map represents the inflow of a contrast agent into the plurality of vessels as a function of time under hyperemic conditions.

The first and second time series should be acquired under different conditions, such as to obtain two comparable datasets. In some embodiments, these different conditions may particularly refer to the condition of a patient. In some embodiments, one of the two conditions may be a condition of a patient, where the patient is in a resting state and the other one of the two conditions may be a condition of a patient, where the patient is in a hyperemic state. This hyperemic state may particularly be induced by administering a vasodilatory agent to the patient.

In this embodiment, the global hemodynamic parameter is determined based on two time-resolved measurements for establishing the contrast agent evolution through the vasculature over time under two different physical conditions. That is, in both cases a vessel map feature is regarded which value is constantly rising, with the difference between the value for the two different physiological states being indicative of a flow-related global hemodynamic parameter.

In some embodiments, the first dynamic vessel map represents the inflow of a contrast agent into the plurality of vessels as a function of time and the second dynamic vessel map represents the outflow of a contrast agent into the plurality of vessels as a function of time.

In some embodiments, the condition may be a condition of the contrast agent dynamics. In some embodiments, the first time series of diagnostic images may particularly be acquired during inflow of the contrast agent into the vasculature and the second time series of diagnostic images may be acquired during outflow. In order to improve reliability and comparability for this particular embodiment, the contrast agent infusion rate should be known, as should be the bolus length.

In this embodiment, the patient may particularly be in a contrast-induced hyperemic state, that is, the hyperemia is caused by the contrast agent inside the vessels. In this case, the first time series tracks the growing of the vessel map visualized in the diagnostic image and the second time series tracks the decrease thereof. For both cases respective vessel map feature values are acquired and subsequently compared.

In some embodiments, the first time series of vessel map feature values comprises a first plurality of values indicative of an area occupied by the plurality of vessels in each diagnostic image of the first time series of diagnostic images as a function of time and the second time series of vessel map feature values comprises a second plurality of values indicative of an area occupied by the plurality of vessels in each diagnostic image of the second time series of diagnostic images as a function of time.

In some embodiments, the feature of the vessel map may particularly refer to the area occupied by the vessels of the vasculature to be examined in the diagnostic images. That is, in these embodiments it is determined, for each diagnostic image, i.e. for each point in (measurement) time, a value indicating how much of the area of the image is occupied by the vessels. This area should increase with contrast agent inflow and decrease with contrast agent outflow, thereby allowing to draw conclusions about the contrast agent dynamics.

It shall be understood that the value indicating the area occupied by the vessels may particularly be a relative value, where 0.0 means that no area is occupied and 1.0 means that the entire diagnostic image area is covered by the vessels. It shall further be understood that the relative value may not be determined for the entire diagnostic image area, but may also be determined for a section of said diagnostic image area, e.g. for the inner 90% to 70% of the diagnostic image area.

To that end, a value indicating the area occupied by the vessels in the diagnostic image shall be acquired for each diagnostic image of the first time series and for each diagnostic image of the second time series. In order to keep these values comparable, the diagnostic image area or a section thereof has to be selected equally for both time series. This allows to obtain accurate information about the contrast inflow (or outflow) and, by that, about the global flow dynamics inside the vessels in the vasculature.

In some embodiments, the analyzation unit is configured to compare the first time series of vessel map feature values and the second time series of vessel map feature values by determining a first slope value for the first plurality of values indicative of the area occupied by the plurality of vessels as function of time, determining a second slope value for the second plurality of values indicative of the area occupied by the plurality of vessels as function of time, and comparing the first and second slope value to derive the at least one global hemodynamic parameter.

In some embodiments, the determination of the at least one global hemodynamic parameter may particularly be based on a comparison of a slope value indicating the slope of the area occupied by the vessels as a function of time for the first time series and the second time series respectively. For this purpose, the values determined per diagnostic image of both time series for the area occupied by the vessels are regarded as a function of time, i.e. a course of these values is calculated as a function of measurement time, whereby the measurement time is determined relative to the time point of injection of the contrast agent or to the time point of start of the contrast agent outflow. Subsequently, for each diagnostic image, a slope value is determined. This slope value may particularly correspond to a maximum slope or an average slope. The thus determined slope values (determined for each one of the diagnostic images acquired at a particular point in time) are compared for both time series. That is, the slope value determined for one particular diagnostic image of the first time series acquired at one particular point in measurement time relative to the injection of the contrast agent is compared to the slope value determined for the corresponding diagnostic image of the second time series acquired at the corresponding point in measurement time, i.e. relative to the injection of the contrast agent or the start of the outflow of the contrast agent. Based on this comparison, differences between the slope under different conditions may be determined, thereby allowing to draw conclusions regarding the flow dynamics inside the vessels.

In some embodiments, the analyzation unit further comprises a classifier unit trained with a ground truth for the at least one global hemodynamic parameter, wherein the classifier unit is configured to derive, based on the comparing and the ground truth, the at least one global hemodynamic parameter.

In some embodiments, the analyzation unit implements a machine learning algorithm. That is, the analyzation unit comprises a classifier unit that has been trained with a ground truth relating to the slope comparison and the respective global hemodynamic parameter values of interest. The training of the classifier may particularly be performed using a training dataset that has been derived from previous measurements of the same patient or of a plurality of different patients. Based on this ground truth, the analyzation unit is enabled to obtain the at least one global hemodynamic parameter using an empirical function, by comparison of the slope of the vessel area occupied in the image as a function of time under resting conditions and hyperemic conditions, respectively.

In some embodiments, the input unit is further configured to receive first intravascular measurement data comprising a first pressure value acquired under resting conditions at a proximal measurement position inside a vessel of interest of the plurality of vessels and receive second intravascular measurement data comprising a first pressure value acquired under hyperemic conditions at the proximal measurement position inside the vessel of interest and the apparatus further comprises a comparing unit configured to determine a deviation between the first pressure value acquired under resting conditions and the first pressure value acquired under hyperemic conditions, compare the deviation to a predetermined threshold and, if the deviation is larger than the predetermined threshold, output a corresponding indication.

The accuracy of the at least one global hemodynamic parameter is an important factor in the assessment of coronary artery disease. Thus, in some embodiments, an approach is implemented with allows to detect potential inaccuracies/unreliability of the at least one global hemodynamic parameter determined by the analyzation unit.

In some embodiments, the catheter used for injecting the contrast agent into the vasculature may allow to determine an aortic pressure value in the vessel in which the catheter is introduced. That is, the catheter is introduced into the vessel and positioned at a first measurement position, which corresponds to a proximal position, and used to obtain a pressure value at this position under both, resting and hyperemic conditions. This is achieved by means of a pressure sensor connected to the outside of the injection catheter, whereby the pressure propagates through the hollow length of the injection catheter. In some embodiments, the pressure measurement is not performed by the catheter, but by an additional pressure wire introduced into a vessel of interest.

In that context, the term proximal shall be understood within its conventional meaning, i.e. as defining a position close to the main mass of the body. In terms of coronary vessels, a proximal position is a position closer to the heart, typically close to the aorta, than a respective distal position when viewed along a longitudinal axis of the coronary vessel. Accordingly, the term proximal measurement position particularly may refer to an intravascular position relatively close to or in the aorta, at which a pressure value is measured by an invasive measurement. This pressure value is hereby measured once under resting conditions and once under hyperemic conditions at the same proximal measurement position.

These pressure values obtained by the catheter at the proximal measurement position are then compared to one another to detect if a significant change in (aortic) pressure or heart rate has occurred between the measurement under resting conditions and the measurement under hyperemic conditions. That is, a deviation between the pressure values obtained under resting and hyperemic conditions, respectively, is compared to a predetermined threshold. If it is determined that the deviation exceeds the threshold, an indication thereof is generated. A suitable threshold for this measure might lie within the range of 15 to 5 mmHg. A particular threshold may hereby be 10 mmHg.

In this context, the term indication may refer to a warning that is output to a user to inform the user about the occurrence of the deviation. In some embodiments, the term indication may alternatively or additionally refer to a correction factor that is generated and provided to the analyzation unit to correct the at least one global hemodynamic parameter. This correction factor may particularly be provided in terms of a training- or model-based correction.

In accordance with these embodiments, inaccuracies in the determined global hemodynamic parameters may be reduced and/or the user may be warned if there is potential for such inaccuracies, thereby improving the assessment process.

In some embodiments, the first intravascular measurement data further comprises a second pressure value acquired under resting conditions at a distal measurement position inside the vessel of interest, and the second intravascular measurement data further comprises a second pressure value acquired under hyperemic conditions at the distal measurement position inside the vessel of interest. The apparatus further comprises a determination unit configured to determine a value indicative of a hydrostatic pressure difference between the proximal measurement position and the distal measurement position inside the vessel of interest and a calculation unit configured to calculate, based on the first and second pressure value of the first intravascular measurement data, the first and second pressure value of the second intravascular measurement data and the value indicative of the hydrostatic pressure difference, at least one local hemodynamic parameter. In some embodiments, the at least one value indicative of the hydrostatic pressure difference comprises a height difference between the proximal measurement position and the distal measurement position. In some embodiments the at least one local hemodynamic parameter comprises a coronary flow reserve (CFR).

The above-cited embodiments allow for the determination of a global hemodynamic parameter. This global hemodynamic parameter is typically a flow-related hemodynamic parameter, i.e. a hemodynamic parameter that globally assesses the flow dynamics in the vasculature of interest. In some embodiments, it may also be useful to perform local assessment of specific vessels in the vasculature. This may particularly be the case, if a vessel is identified has having a steno sis or the like. Thus, it may be desirable to determine at least one local hemodynamic parameter. More specifically, it may be desirable to determine at least one local flow-related hemodynamic parameter. Even more specifically, a local value for the coronary flow reserve may be determined.

Hereby, determination of the clinically very helpful hemodynamic parameter coronary flow reserve (CFR) is often desired. The CFR is defined as the ratio of the hyperemic flow velocity $v_H$ and the resting flow velocity $v_R$:

$$CFR = \frac{v_H}{v_R}.$$

Thus, in order to determine the CFR, flow measurements for determining the flow velocity have to be performed under hyperemic and resting conditions, respectively. To that end, it was not possible to allow the determination of CFR using pressure measurements. This is so since the pressure gradient between the pressure values at two measurement positions inside a vessel is influenced by two factors, the friction losses in the vessel and by a hydrostatic pressure difference which occurs since the two measurements are typically not performed at the same elevation. That is, according to Bernoulli's principle, the measured pressure gradient may be described as:

$$\Delta p_{meas} = \rho * g * \Delta h + \Delta p_{friction} + 1/2 * \rho * (v_1^2 - v_2^2),$$

where $\rho$ is the blood density, g is the gravitational constant, $\Delta h$ corresponds to the difference in elevation (or height difference) and $v_1$ and $v_2$ are the respective flow velocities at the measurement positions where the pressure measurement was performed. The pressure gradient $\Delta p_{Bernoulli}$ $1/2 * \rho * (v_1^2 - v_2^2)$ is typically negligible, since the flow velocities are usually very similar. The friction losses in the vessel are correlated to the flow velocity according to $$\Delta p_{friction} = R * v,$$

where R describing the fluid dynamic resistance of the particular vessel of interest and v corresponding to the flow velocity. Thus, since $$CFR = \frac{v_H}{v_R}$$

and $\Delta p_{friction} = R*v$, one may derive $$CFR = \frac{\Delta p_{friction\_H}}{\Delta p_{friction\_R}} = \frac{R*v_H}{R*v_R}$$

Thus, in order to determine a CFR locally in the vessel of interest, it is necessary to separate the hydrostatic contribution and the friction-related contribution of the pressure measurement from one another.

In order to achieve this object, the information obtained using intravascular pressure measurements is combined with a value indicative of a hydrostatic pressure difference retrieved by means of a further medical measurement modality. To that end, suitable medical measurement modalities particularly encompass computed tomography, X-ray angiography or any type of three-dimensional tracking of the pressure wire, such as electromagnetic tracking, ultrasound tracking, impedance-based tracking or the like. Further, optical shape sensing may also be employed to determine the value.

The intravascular measurements may hereby particularly be performed, under both, hyperemic and resting conditions, whereby for both cases at least two pressure values are determined, one at a proximal and one at a distal measurement position. This allows to determine the pressure difference between the proximal and distal measurement position under hyperemic conditions as well as resting conditions. These intravascular pressure measurements may particularly be performed by means of a pressure wire that is introduced into the vessel of interest. The pressure wire is used to measure a pressure value at at least two measurement positions, namely the proximal measurement position and a distal measurement position. The term distal measurement position hereby refers to an intravascular position inside the vessel of interest, which is distant from the main mass of the body. That is, for the coronary vasculature, a distal position relates to a position more distant from the heart compared to the proximal position when viewed along a longitudinal axis of the coronary vessel.

That is, two sets of intravascular measurement data are obtained. The first intravascular measurement data hereby comprises the first and second pressure value obtained at the proximal and distal measurement position, respectively, under resting conditions. The second intravascular measurement data comprises the first and second pressure value obtained at the proximal and distal measurement position under hyperemic conditions.

These two sets of intravascular measurement data are then provided to a determination unit. The determination unit further receives measurement data from the additional medical measurement modality. This measurement data may particularly refer to one or more tracking images and/or one or more diagnostic images, whereby the value indicative of the hydrostatic pressure difference may be derived from these images. As an example, an electromagnetic tracking image is obtained. The determination unit then uses this electromagnetic tracking image to determine the value indicative of the hydrostatic pressure difference. Such a value indicative of the pressure difference may hereby particularly be a height difference Δh.

Hereby, the elevation, i.e. the determination of the height difference Δh shall particularly be performed at least across a cardiac cycle in order to correct the hemostatic effects in their variability during the cardiac cycle. In some embodiments, where wire tracking is used, and, thus, the elevation is continuously tracked, a motion correction to correct for the variability of the height difference Δh due to breathing motion may also be performed.

If the height difference Δh is known, it is possible to approximate $\Delta p_{friction}$ as $\Delta p_{friction} = \Delta p_{meas} - \rho * g * \Delta h$. This allows to determine the CFR according to:

$$CFR = \frac{\Delta p_{meas\_H} - \rho * g * \Delta h}{\Delta p_{meas\_R} - \rho * g * \Delta h}$$

By means of this approximation, it is possible to derive a local CFR value as a flow-related index from respective pressure measurements.

As may be appreciated from the above, this determination of the local CFR value does not require a previous determination of a global CFR value as also performed by the apparatus. What is necessary is that the apparatus is provided with first and second intravascular measurement data measured at a proximal and distal measurement position under resting and hyperemic conditions, respectively, and measurement data which allows to determine the elevation between the two measurement positions.

In some embodiments, the determining of the value indicative of the hydrostatic pressure difference is performed based on at least one diagnostic image obtained from at least one of the first time series of diagnostic images and the second time series of diagnostic images.

In some embodiments, the determination unit may particularly use at least one diagnostic image from the first time series and/or the second time series. The benefit of this approach would be that this is already readily available to the apparatus. Hereby, the diagnostic image data may particularly be a single or multiple angiography images taken at specific projection angles. In some embodiments, further diagnostic image data may be used, such as a CT model.

According to a further aspect, a method for assessing a coronary vasculature is provided, the method comprising the steps of receiving a first time series of diagnostic images of a plurality of vessels in the coronary vasculature, receiving a second time series of diagnostic images of the plurality of vessels in the coronary vasculature, the first time series and the second time series having been acquired with different acquisition conditions, whereby each one of the diagnostic images of the first time series and each one of the diagnostic images of the second time series respectively represents a visualization of a contrast agent dynamics for a particular point in time, computing, for the first time series of diagnostic images, a first time series of vessel map feature values of a first dynamic vessel map representing the plurality of vessels, computing, for the second time series of diagnostic images, a second time series of vessel map feature values of a second dynamic vessel map representing the plurality of vessels, the first time series of vessel map feature values and the second time series of vessel map feature values being indicative of the contrast agent evolution over time, comparing the first time series of vessel map feature values and the second time series of vessel map feature values, and deriving, based on the comparing, at least one global hemodynamic parameter.

In some embodiments, the method further comprises the steps of receiving first intravascular measurement data comprising a first pressure value acquired under resting conditions at a proximal measurement position inside a vessel of interest of the plurality of vessels and a second pressure value acquired under resting conditions at a distal measurement position inside the vessel of interest, receiving second intravascular measurement data comprising a first pressure value acquired under hyperemic conditions at the proximal measurement position inside the vessel of interest and a second pressure value acquired under hyperemic conditions at the distal measurement position inside the vessel of interest, determining, based on at least one diagnostic image obtained from at least one of the first time series of diagnostic images and the second time series of diagnostic images, a value indicative of a hydrostatic pressure difference between the proximal measurement position and the distal measurement position inside the vessel of interest and calculating, based on the first and second pressure value of the first intravascular measurement data, the first and second pressure value of the second intravascular measurement data and the value indicative of the hydrostatic pressure difference, at least one local hemodynamic parameter.

In a further aspect, a computer program for controlling an apparatus according to any of the above embodiments is provided, which, when executed by a processing unit, is adapted to perform the method according to one or more of its embodiments. In an even further aspect, a computer-readable medium having stored thereon the computer program is provided.

It shall be understood that the apparatus of claim 1, the method of claim 12, the computer program according to 14, and the computer readable medium of claim 15, have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
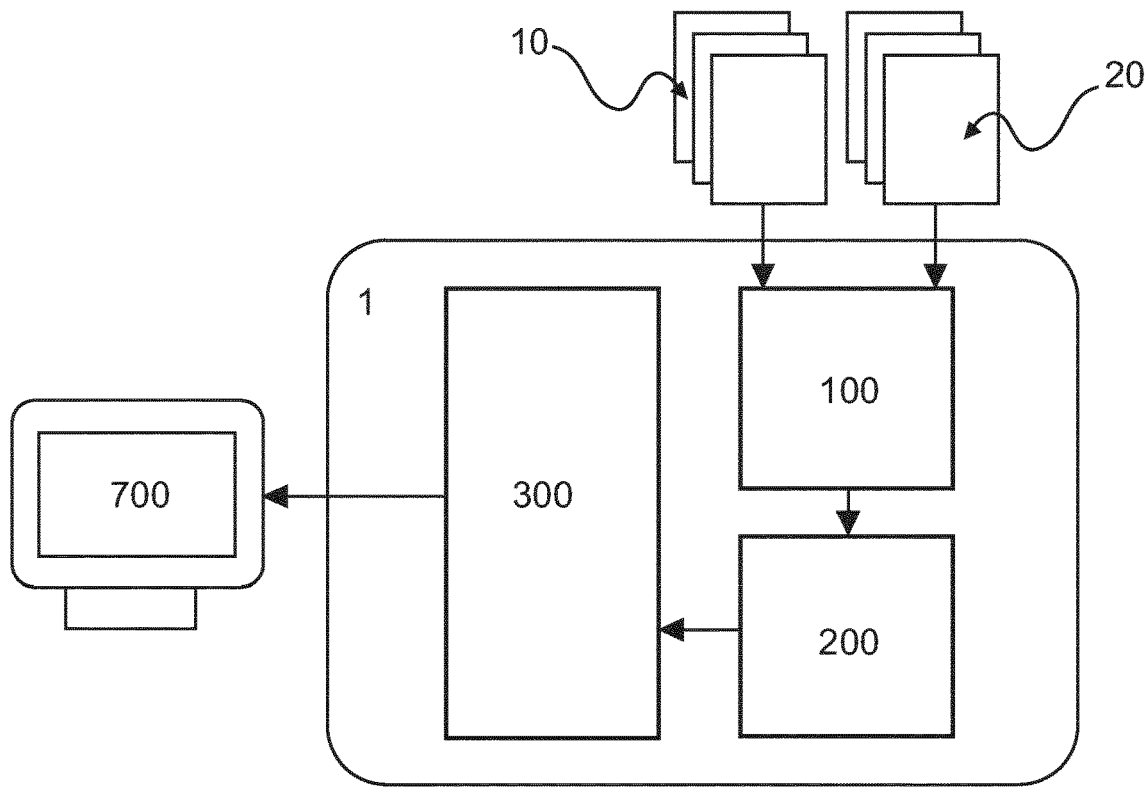
FIG. 1 schematically illustrates an apparatus for assessing a coronary vasculature according to a first exemplary embodiment.

The illustration in the drawings is schematically. In different drawings, similar or identical elements are provided with the same reference numerals.

FIG. 1 represents schematically a first exemplary embodiment of an apparatus 1 for determining at least one global hemodynamic parameter in order to assess the coronary vasculature. Apparatus 1 comprises an input unit 100, a computation unit 200 and an analyzation unit 300 and is communicatively coupled to display unit 700.

Input unit 100 is configured to receive a first time series 10 of diagnostic images and a second time series 20 of diagnostic images from a medical imaging modality. In the exemplary embodiment of FIG. 1, the first time series 10 is acquired under resting conditions, i.e. while the patient is at rest. The second time series 20 is acquired under hyperemic conditions, i.e. the patient received a vasodilatory agent to induce hyperemia.

In the exemplary embodiment according to FIG. 1, the first time series 10 and second time series 20 each comprise a plurality of diagnostic images collected during contrast agent inflow using invasive X-ray angiography. The contrast agent is hereby introduced by inserting a contrast injection catheter into a vessel in a patient's coronary vasculature and injecting the contrast agent using this catheter.

The acquisition of the first time series 10 of diagnostic images is hereby optionally started concurrently with the starting of the injection of the contrast agent into the vasculature and stopped once the contrast agent has been completely injected. That is, the first time series 10 shows the full inflow of the contrast agent into the coronary vasculature under resting conditions and the second time series 20 shows the full inflow of the contrast agent under hyperemic conditions.

The first time series 10 and second time series 20 are then provided to computation unit 200. Computation unit 200 is configured to receive the first time series 10 and the second time series 20 and, in the exemplary embodiment according to FIG. 1, applies a coarse segmentation to each diagnostic image of the first time series 10 and of the second time series 20. This segmentation allows to determine a vessel map feature for each diagnostic image in the first time series 10 and the second time series 20, respectively.

In the exemplary embodiment according to FIG. 1, this vessel map feature particularly is a vessel area that is occupied by the vessels in a predefined portion of the diagnostic image (i.e. that is visualized due to contrast agent having already entered a particular part of the vasculature). Accordingly, a value for the vessel map area is calculated for each diagnostic image in the first time series 10 and the second time series 20. These values are then provided to analyzation unit 300.

Analyzation unit 300 is configured to consider each value for the vessel map area in the diagnostic images of the first time series 10 as a function of time and each value for the vessel map area in the diagnostic images of the second time series 20 as a function of time. That is, analyzation unit 300 determines two mappings for the vessel map area values, one for the first time series 10 and one for the second time series 20. This enables the analyzation unit 300 to derive a slope for both mappings and to compare the slope of these functions to one another. In the exemplary embodiment of FIG. 1, analyzation unit hereby determines the maximal slope and compares the maximal slope for the vessel map area of the first time series 10 to the maximal slope for the vessel map area of the second time series to determine a global flow-related hemodynamic parameter, which, in the exemplary embodiment of FIG. 1, is a global value for the coronary flow reserve (CFR). It shall be understood that, in some embodiments, the average slope may be used to determine the global flow-related hemodynamic parameter, such as the CFR.

For this purpose, the analyzation unit 300 may optionally implement a machine-learning algorithm. That is, the analyzation unit 300 may comprise a classifier unit that has been trained with a ground truth relating to the slope relation and the respective global CFR values (or other global hemodynamic parameter values) using a training dataset derived e.g. from a plurality of different patients. Based on this ground truth, the analyzation unit then determines a respective global CFR value indicated by the comparison of the slope of the vessel area occupied in the image as a function of time at a resting state and a hyperemic state, respectively. The analyzation unit optionally provides the determined global CFR value to display unit 700.

Display unit 700 computes a graphical representation of the determined global CFR value and provides this representation to a user.

Figure 2:
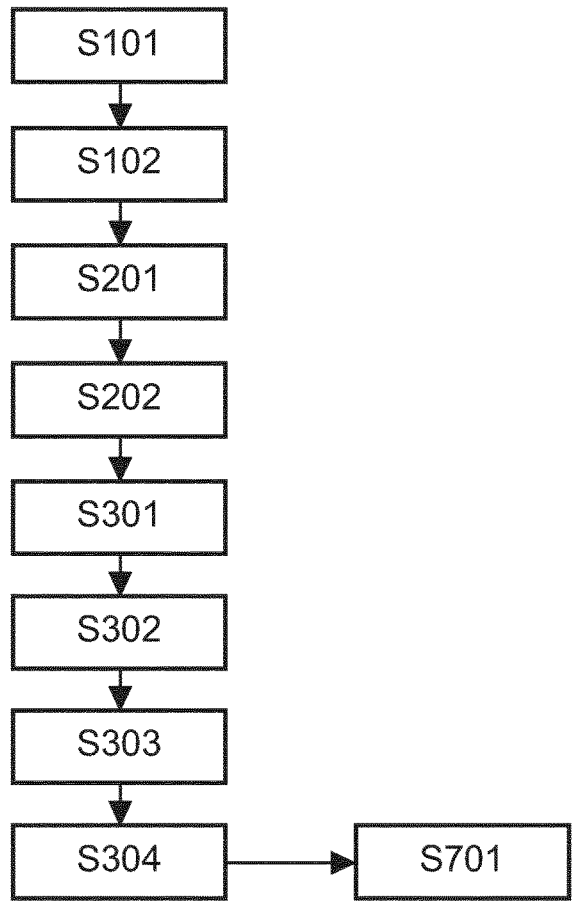
FIG. 2 represents a flow chart for a method for assessing a coronary vasculature according to the first exemplary embodiment.

FIG. 2 represents schematically a flow chart of the method for determining a global flow-related hemodynamic parameter using apparatus 1 according to the exemplary embodiment of FIG. 1.

In step S101, input unit 100 receives a first time series 10 of diagnostic images, the first time series 10 having been acquired under resting conditions. In step S102, input unit 100 further receives a second time series 20 of diagnostic images, having been acquired under hyperemic conditions.

In step S201, computation unit 200 receives the first time series 10 of diagnostic images and applies a coarse segmentation to each diagnostic image of the first time series 10 to determine a vessel map feature value for each diagnostic image, i.e. a value representing the time evolution of the feature map. In step S202, computation unit 200 receives the second time series 20 of diagnostic images and applies a coarse segmentation to each diagnostic image of the second time series to determine a respective vessel map feature value for each diagnostic image. As indicated herein above, in the exemplary embodiment, the vessel map feature is the area that is occupied by the vessels in a predefined portion of the diagnostic images. Thus, a value for the vessel map area is calculated for each diagnostic image in the first time series 10 and the second time series 20 in steps S201 and S202 and subsequently provided to analyzation unit 300.

In step S301, analyzation unit 300 determines a mapping for the values representing the area occupied by the vessels in the diagnostic images of the first time series 10 by considering each value determined for the first time series as a function of time to derive a first slope for the time series of these values. In the exemplary embodiment of FIG. 2, this first slope is a maximal slope. In step S302 analyzation unit 300 determines a mapping for the values representing the area occupied by the vessels in the diagnostic images of the second time series 10 by considering each value for the second time series 20 as a function of time to derive a second slope of the time series of these values. In the exemplary embodiment of FIG. 2, this second slope is also a maximal slope.

In step S303, analyzation unit 300 compares the first and second maximal slope to one another. In step S304, analyzation unit 300 uses the comparison to determine a global flow-related hemodynamic parameter, such as the coronary flow reserve (CFR). In step S701, a graphical representation of the result of this determination is generated by display unit 700 and presented to a user.

Figure 3:
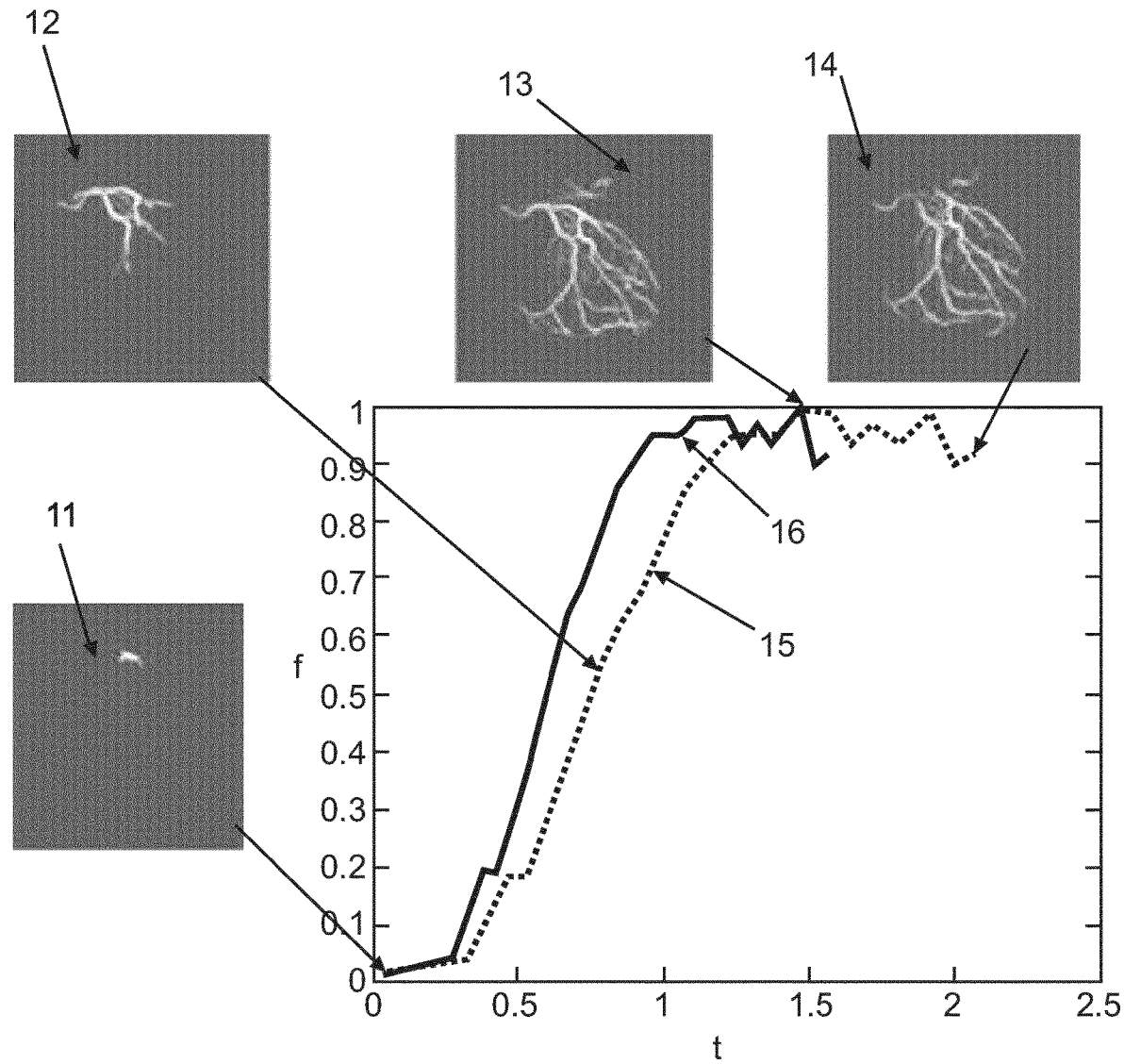
FIG. 3 illustrates a graphical representation of a determination of a flow-related hemodynamic parameter according to the first exemplary embodiment.

FIG. 3 illustrates a graphical representation of a determination of a flow-related hemodynamic parameter according to the first exemplary embodiment. Diagnostic images 11, 12, 13 and 14 visualize the vessel map evolution during contrast agent injection over time for a resting condition. It shall be understood that the diagnostic images for a hyperemic conditions would visualize the vessel map in a corresponding manner.

Diagnostic image 11 only shows a small part of the vessel map, i.e. the area occupied by the vessel map in the diagnostic image 11 has a relatively small value. In contrast, diagnostic image 14, which was acquired at full inflow of the contrast agent, visualizes a large vessel map, i.e. the area occupied by the vessel map in the diagnostic image 14 has a relatively large value.

In order to properly track the contrast agent dynamic under resting conditions, curve 15 is determined, in which the values for the area occupied by the vessel map in the diagnostic images is computed as a function of time. Further, in order to track the contrast agent dynamic under hyperemic conditions, curve 16 is provided, in which the corresponding values for the area occupied by the vessel map in the diagnostic images is also computed as a function of time. This allows to derive a slope value for both curves. The slope value may then be used to determine the global flow-related hemodynamic parameter.

Figure 4:
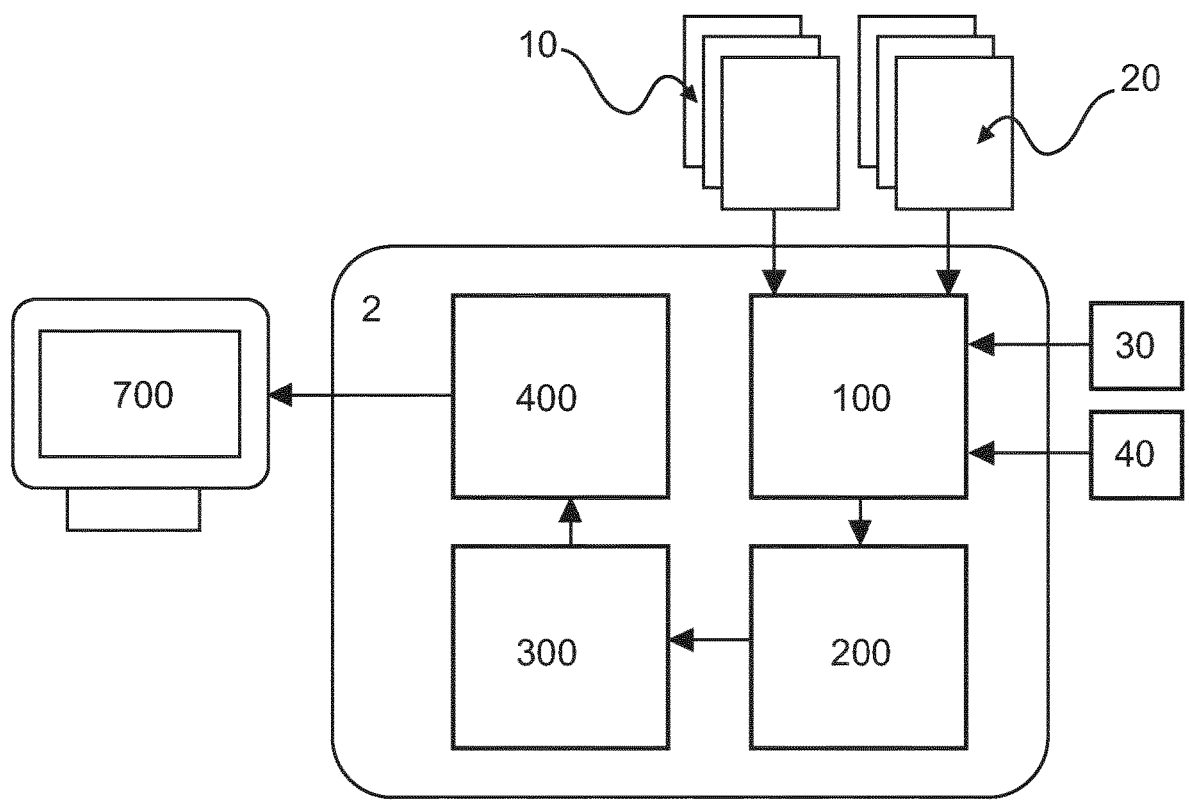
FIG. 4 schematically illustrates an apparatus for assessing a coronary vasculature according to a second exemplary embodiment.

FIG. 4 schematically illustrates an apparatus 2 for assessing a coronary vasculature according to a second exemplary embodiment. Apparatus 2 comprises an input unit 100, a computation unit 200, an analyzation unit 300 and a comparing unit 400 and is communicatively coupled to a display unit 700.

In the exemplary embodiment of FIG. 4, the input unit 100 is configured to receive a first time series 10 of diagnostic images and a second time series 20 of diagnostic images from a medical imaging modality and to further receive first intravascular measurement data 30 comprising a first pressure value determined by an intravascular measurement device at a proximal position inside the vessel and second intravascular measurement data 40 comprising a second pressure value determined by an intravascular measurement device at a proximal position inside the vessel. In the exemplary embodiment according to FIG. 4, the intravascular measurement device may particularly be the injection catheter for injection of the contrast agent.

Hereby, the first time series 10 of diagnostic images and the first intravascular measurement data 30 are acquired under resting conditions. That is, the first intravascular measurement data 30 determined using the catheter when injecting the contrast agent for collection of the first time series 10. Similarly, the second time series 20 of diagnostic images and the second intravascular measurement data 40 are acquired under hyperemic conditions, i.e. the second intravascular measurement data 30 is determined using the catheter for contrast agent injection for collection of the second time series 20.

The first time series 10 and the second time series 20 are then provided to computation unit 200 for coarse segmentation as described in relation to FIG. 1 in order to compute a first time series of vessel map feature values and a second time series of vessel map feature values, respectively. The thus computed first and second time series of vessel map feature values are subsequently provided to analyzation unit 300 and analyzed therein as also described in relation to FIG. 1. That is, analyzation unit 300 considers each value for the vessel map area in the diagnostic images of the first time series 10 as a function of time and each value for the vessel map area in the diagnostic images of the second time series 20 as a function of time, derives a slope for both curves and compares the slope for both curves to one another to determine a global flow-related hemodynamic parameter, which, in the exemplary embodiment of FIG. 4, is a global CFR value.

The first intravascular measurement data 30 comprising a first pressure value acquired under resting conditions and the second intravascular measurement data 40 comprising a first pressure value acquired under hyperemic conditions are provided to the comparing unit 400. Comparing unit 400 compares the first pressure value acquired under resting conditions and the second pressure value acquired under hyperemic conditions and determines if there is a deviation between these values. More specifically, comparing unit 400 determines a value for this deviation. Comparing unit 400 then compares this deviation value to a predetermined threshold value. If the value exceeds the threshold value, comparing unit 400 provides an indication thereof.

In the exemplary embodiment of FIG. 4, comparing unit 400 particularly sends an indication to display unit 700 and display unit 700 computes a graphical representation of the indication, such as a warning or an alarm signal, to show the user that the determined global flow-related hemodynamic parameter may be unreliable. Alternatively or additionally, comparing unit may also use the comparison to determine a correction factor and may be configured to apply the correction factor to the determined global hemodynamic parameter in order to overcome the potential unreliability. In that case, an indication that a correction has been performed may be provided to display unit 700 and display unit 700 may generate a graphical representation of that indication, so the user is aware of the correction. To that end, it shall be understood that display unit 700 may also receive the determined global hemodynamic parameter and generate a representation thereof to present to the user.

Figure 5:
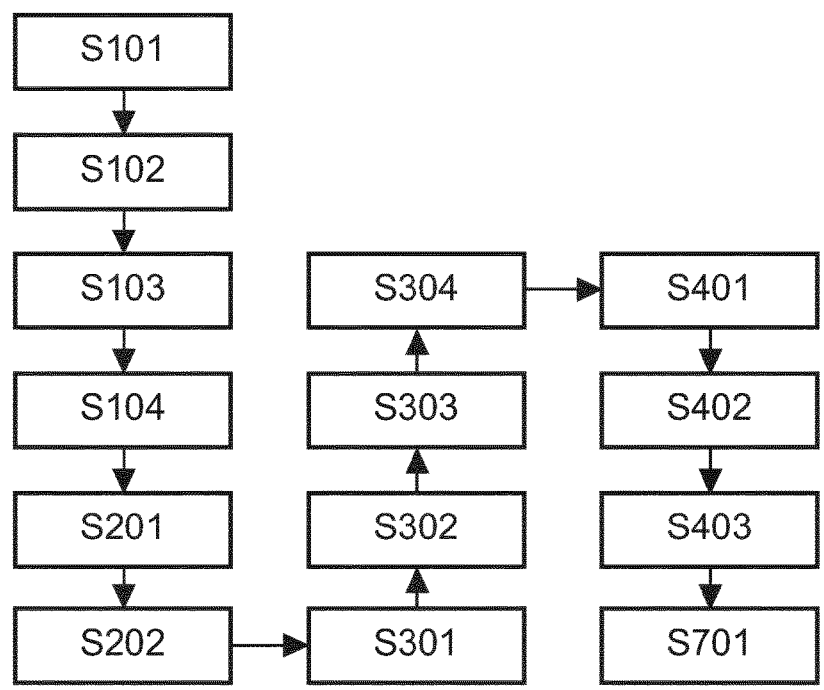
FIG. 5 represents a flow chart for a method for assessing a coronary vasculature according to the second exemplary embodiment.

FIG. 5 represents a flow chart for a method for assessing a coronary vasculature according to the second exemplary embodiment. Steps S101 and S102 correspond to steps S101 and S102 according to the first embodiment and explained in relation to FIG. 2, i.e. in these steps a first time series 10 of diagnostic images and a second time series 20 of diagnostic images from a medical imaging modality are received at the input unit 100. In step S103, the input unit 100 further receives first intravascular measurement data 30 comprising a first pressure value determined at a proximal position inside a vessel under resting conditions. Further, in step S104, input unit 100 receives second intravascular measurement data 40 comprising a first pressure value measured at a proximal position inside the vessel under hyperemic conditions.

In steps S201 to S304 of FIG. 5, the first time series 10 and the second time series 20 processed by computation unit 200 and analyzation unit 300 as described in relation to FIG. 1 in order to determine a global flow-related hemodynamic parameter. This global flow-related hemodynamic parameter may be reliable or unreliable. In order to determine the reliability of the global flow-related hemodynamic parameter, the first and second intravascular measurement data 30, 40 are used by comparing unit 400 in steps S401 to S403.

That is, in step S401, comparing unit 400 compares the first pressure value acquired under resting conditions and the second pressure value acquired under hyperemic conditions and determines a value indicative of the deviation of the two pressure values. In step S402, comparing unit 400 compares this deviation value to a predetermined threshold value and, if the value exceeds the threshold value, provides an indication that the determined global hemodynamic parameter may be unreliable in step S403. This indication may be a warning that can be graphically represented to a user by display unit 700 in step S701.

Alternatively or additionally, the indication may also correspond to a correction factor that can be applied to the global hemodynamic parameter determination in step S403. In that case, the display unit 700 may generate a graphical representation of an indication that a correction has been performed and present said representation to a user in step S701.

Figure 6:
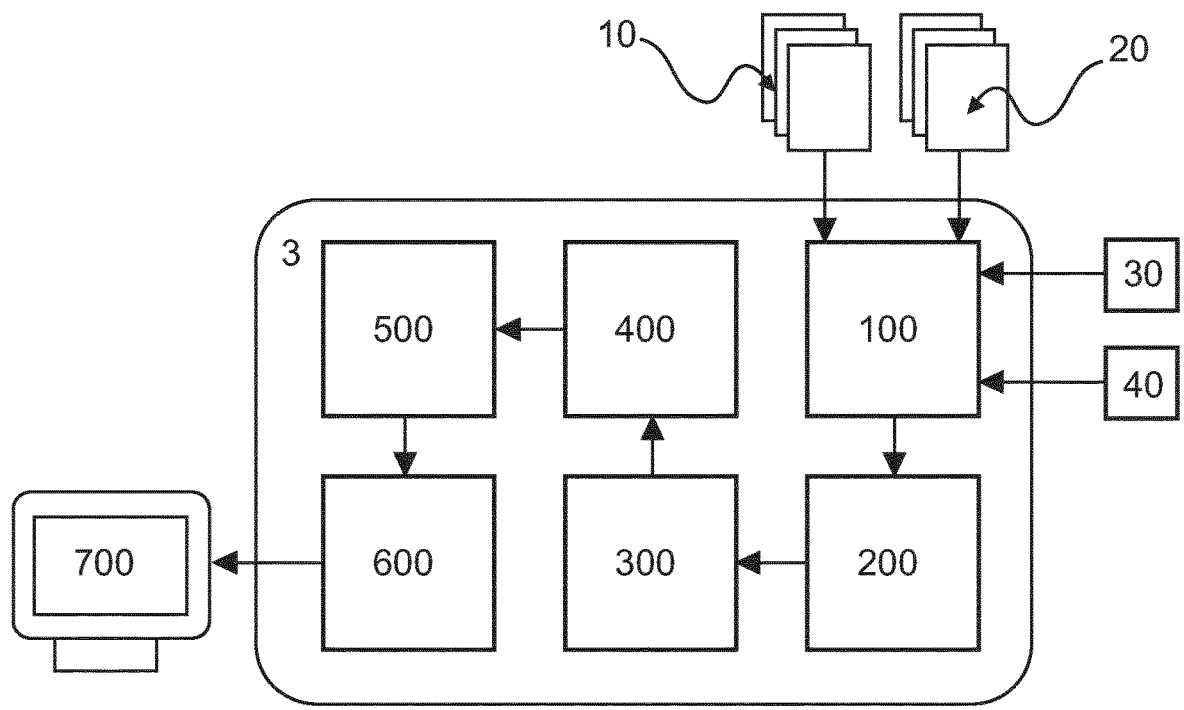
FIG. 6 represents a flow chart for a method for assessing a coronary vasculature according to a third exemplary embodiment.

FIG. 6 schematically illustrates an apparatus 3 for assessing a coronary vasculature according to a third exemplary embodiment. Apparatus 3 also comprises an input unit 100, a computation unit 200, an analyzation unit 300 and a comparing unit 400 and is communicatively coupled to a display unit 700. The respective functionalities of these units correspond to the ones explained in relation to FIG. 4 and will not be discussed in detail in the following to avoid unnecessary repetitions. Further to that, apparatus 3 comprises a determination unit 500 and a calculation unit 600.

In the exemplary embodiment according to FIG. 6, the input unit 100 is configured to receive a first time series 10 of diagnostic images and a second time series 20 of diagnostic images from a medical imaging modality and to further receive first intravascular measurement data 30 and second intravascular measurement data 40. The first intravascular measurement data 30 hereby comprises a first pressure value acquired under resting conditions at a proximal position inside a vessel of interest and a second pressure value acquired under resting conditions at a distal position. Similarly, the second intravascular measurement data 40 comprises a first pressure value acquired under hyperemic conditions at a proximal position inside a vessel of interest and a second pressure value acquired under hyperemic conditions at a distal position. In the exemplary embodiment according to FIG. 6, the first and second intravascular measurement data may particularly have been obtained by inserting a pressure wire into a vessel of interest and measuring the pressure values at two measurement positions, a proximal and a distal position, under resting and hyperemic conditions.

It shall be understood that, alternatively or additionally, the input unit 100 may also receive one or more measurement results from a different medical measurement modality. As an example, the input unit 100 may receive three-dimensional tracking images of a pressure wire for performing the intravascular pressure measurement. In this particular case, the apparatus may even work entirely without receiving the first and second time series of diagnostic images.

The first time series 10 of diagnostic images and the second time series 20 of diagnostic images may be processed by the computation unit 200 and the analyzation unit 300 to determine a global hemodynamic parameter, as described in detail herein above. Further, the first intravascular measurement data 30 and the second intravascular measurement data 40 may optionally be used to provide input on the reliability of the global hemodynamic parameter and/or to correct the global hemodynamic parameter when necessary. For this purpose, the comparing unit 400 compares the first pressure value acquired under resting conditions and the second pressure value acquired under hyperemic conditions and determines if there is a deviation between these values. Comparing unit 400 then compares the value of this deviation to a predetermined threshold value to determine if the threshold is exceeded. If that is the case, an indication is provided which indicates the reliability of the global hemodynamic parameter and may also indicate a correction factor to correct the global hemodynamic parameter.

Further, apparatus 3 comprises a determination unit 500. One or more diagnostic images from the first time series 10 or the second time series 20 are provided to the determination unit 500. Alternatively, one or more tracking images obtained by a respective tracking modality may be provided to determination unit 500. Determination unit 500 segments the diagnostic or tracking images and determines, based on this segmentation, a value indicative of a hydrostatic pressure difference. In some embodiments, the one or more images may be used to generate, based on the segmentation, a geometric three-dimensional model of the vessel of interest. From this model, two positions, one for each pressure sensor, can be determined. This is possible if the pressure sensor is visible in the images from two different angulations. From these two positions, it is possible to determine the value indicative of the hydrostatic pressure difference. In the exemplary embodiment of FIG. 6, this value may particularly be a height difference $\Delta h$ between the proximal measurement position and the distal measurement position inside the vessel. In some embodiments, the height difference may also be determined using a single 2D diagnostic image, such as a single two-dimensional X-ray image. For this purpose, the C-arm for collecting such X-ray images has to have a suitable orientation. Such a suitable orientation is given if one of the two axes of the X-ray detector is parallel to the pull of gravity. In some embodiments, the value indicative of the hydrostatic pressure difference, in particular the height difference, may be determined using a three-dimensional computed tomography (CT) road map, whereby the two intravascular measurement positions are indicated in the road map. The CT anatomy may then be registered to the patient anatomy. The thus determined height difference $\Delta h$ is then provided to calculation unit 600.

Calculation unit 600 receives the height difference $\Delta h$ and, further, the first intravascular measurement data 30 and the second intravascular measurement data 40. The calculation unit 600 extracts, from the first intravascular measurement data 30, the first pressure value determined at the proximal position and the second pressure value determined at the distal position and determines a pressure difference $\Delta p_{meas\_R}$ for the measurement obtained under resting conditions. Further, the calculation unit 600 extracts, from the second intravascular measurement data 40, the first pressure value determined at the proximal position and the second pressure value determined at the distal position and determines a pressure difference $\Delta p_{meas\_H}$ for the measurement obtained under hyperemic conditions.

The calculation unit 600 then uses the height difference $\Delta h$ and the pressure difference $\Delta p_{meas\_R}$ under resting conditions as well as the pressure difference $\Delta p_{meas\_H}$ measured under hyperemic conditions to determine a local flow-related hemodynamic parameter. This local flow-related hemodynamic parameter may particularly correspond to the coronary flow reserve (CFR). To that end, the CFR may be calculated from the above according to:

$$CFR = \frac{\Delta p_{meas\_H} - \rho * g * \Delta h}{\Delta p_{meas\_R} - \rho * g * \Delta h},$$

where $\rho$ is the blood density, g is the gravitational constant.

The thus determined local flow-related hemodynamic parameter is provided to the display unit 700 along with the global flow-related hemodynamic parameter. The display unit 700 is configured to generate a graphical representation of the global hemodynamic parameter and the local hemodynamic parameter, respectively and to present said graphical representation to a user.

Figure 7:
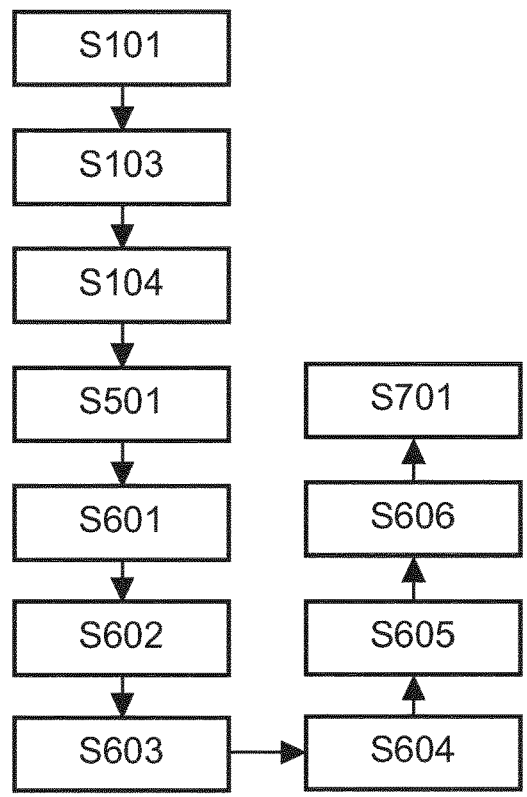
FIG. 7 represents a flow chart for a method for locally determining a flow-related hemodynamic parameter according to an exemplary embodiment.

FIG. 7 represents a flow chart for a method for locally determining a flow-related hemodynamic parameter as described herein above.

In step S101, medical measurement data is received at the input unit 100. This medical measurement data may particularly refer to a diagnostic image or a tracking image, obtained from a vessel of interest. In some embodiments, the diagnostic image may be one of the plurality of diagnostic images in the first time series 10 or one of the plurality of diagnostic images in the second time series 20. In some embodiments, the diagnostic image may be a diagnostic image that has been obtained during a measurement dedicated to obtaining a diagnostic image for the sole purpose of determining the hydrostatic pressure difference and, thus, the local hemodynamic parameter. In some embodiments, the tracking image may be obtained using a 3d-tracking method, such as electromagnetic tracking or optical tracking, for tracking the catheter for introducing the contrast agent. In some embodiments, the tracking image may be obtained using a 3d-tracking method for tracking a dedicated pressure wire.

In steps S103 and S104, the first and second intravascular measurement data is received at the input unit 100, respectively. The first and second intravascular measurement data each comprise a first pressure value measured at a proximal measurement position and a second pressure value measured at a distal measurement position, whereby the first intravascular measurement data has been acquired under resting conditions and the second intravascular measurement data has been acquired under hyperemic conditions.

In step S501, the medical measurement data, in particular the diagnostic or tracking image is segmented at determination unit 500 and, based on this segmentation, a value indicative of a hydrostatic pressure difference is determined. In the exemplary embodiment of FIG. 7, this value corresponds to the height difference $\Delta h$ between the proximal measurement position at which the first pressure value was measured and the distal measurement position at which the second pressure value was measured. The thus determined height difference $\Delta h$ is then provided to calculation unit 600.

In step S601, the calculation unit 600 extracts, from the first intravascular measurement data 30, the first pressure value determined at the proximal position and the second pressure value determined at the distal position. In step S602, the calculation unit then determines a pressure difference $\Delta p_{meas\_R}$ between the first pressure value and the second pressure value of the first intravascular measurement data. That is, the pressure difference for the pressure measurement under resting conditions is obtained in step S602.

In step S604, the calculation unit 600 extracts, from the second intravascular measurement data 40, the first pressure value determined at the proximal position and the second pressure value determined at the distal position. In step S605, the calculation unit then determines the corresponding pressure difference $\Delta p_{meas\_H}$ for the measurement performed under hyperemic conditions.

In step S606, the calculation unit determines a local flow-related hemodynamic parameter based on the height difference $\Delta h$, the pressure difference $\Delta p_{meas\_R}$ under resting conditions and the pressure difference $\Delta p_{meas\_H}$ measured under hyperemic conditions. In the particular embodiment according to FIG. 7, this local flow-related hemodynamic parameter corresponds to the coronary flow reserve (CFR) and is calculated as indicated herein above. The resulting CFR value is then provided to a display unit 700 in step S701 which generates and displays a graphical representation thereof to a user.

Although in above described embodiments, the diagnostic images have been obtained using X-ray angiography, it shall be understood that in other embodiments, the diagnostic images may be retrieved by other imaging methods, such as helical computed tomography or sequential computed tomography, magnetic resonance imaging, ultrasound imaging, or the like.

Further, it shall be understood that, although in the above embodiments, the input unit, the computation unit, the analyzation unit, the comparing unit, the determination unit and the calculation unit are implemented as several separate entities, these units may also correspond to the same entity. More specifically, they may be implemented as respective modules and/or a computer program to be executed by a processing device.

Further, while in the above embodiments, the assessment has been performed for the coronary physiology, in other embodiments, the modeling may likewise be performed on other physiologies of the human body. As an example, the approach may be applied to assess the peripheral arteries in the human body.

It may further be understood that while in the above-embodiments, the first and second time series have been obtained under resting and hyperemic conditions, the first and second time series may also be obtained to correspond to other different conditions, such as the inflow and outflow of the contrast agent from the vasculature.

Further, it shall be understood that, although in the above embodiments, the global hemodynamic parameter is determined per vessel tree (left/right), the apparatus can also be implemented to include a contrast agent injection into sub-branches (such as the LAD/LCX) or may include a segmentation scheme to allow to determine a global hemodynamic parameter per vascular area. Hereby, it shall be understood that the segmentation scheme may cover an explicit vessel segmentation at peak filling of the contrast agent to determine the global hemodynamic parameter per vessel segment or an analysis of the vessel map on a regional basis.

Although in the above embodiments, the slope was used to determine a global hemodynamic value, it shall be understood that the slope may also be used for other applications such as estimation of steno sis severity by adding the slope to the model.

Although in the above embodiments, the pressure measurements were used to determine the coronary flow reserve, it shall be understood that the measurements may also be used to determine, based on a vessel segmentation, values such as the fluid dynamic resistance of the vessel and, therefrom, a corresponding flow velocity value.

Further, it shall be understood that the vessel segmentation may also be used to determine local vessel diameters and, thereby, the pressure gradient $\Delta p_{Bernoulli}$ $1/2*\rho*(v_1^2-v_2^2)$ may be estimated to further improve the accuracy of the pressure-based determination of the CFR.

Although in the above embodiments, only two pressure values have been obtained per intravascular pressure measurement, it shall be understood that the method is equally applicable to pressure pullback data which subsequently allows to determine a CFR pullback dataset.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage. Procedures like the receiving of the time series of diagnostic images and/or of intravascular measurement data, the calculation of the time series of vessel map features, the comparing of feature values, the deriving of the global hemodynamic parameter, the deriving of a local hemodynamic parameter et cetera performed by one or several units or devices can be performed by any other number of units or devices. These procedures in accordance with the invention can hereby be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an apparatus for assessing a coronary vasculature, comprising an input unit configured to receive a first time series of diagnostic images of a plurality of vessels in the coronary vasculature, and a second time series of diagnostic images of the plurality of vessels in the coronary vasculature, a computation unit configured to compute, for the first time series of diagnostic images, a first time series of vessel map feature values of a first dynamic vessel map representing the plurality of vessels, and compute, for the second time series of diagnostic images, a second time series of vessel map feature values of a second dynamic vessel map representing the plurality of vessels and an analyzation unit configured to compare the first time series of vessel map feature values and the second time series of vessel map feature values and to derive, based on the comparing, at least one global hemodynamic parameter.

By means of this arrangement, a global assessment of coronary artery disease is enabled which allows to determine respective global flow-related hemodynamic parameter directly from time sequences of diagnostic images without the need to segment and detect individual vessels.

The invention claimed is:

1. An apparatus for assessing a coronary vasculature of a patient, the apparatus comprising:
 a processor configured to:

receive a first time series of diagnostic images of a plurality of vessels in the coronary vasculature under a first acquisition condition, receive a second time series of diagnostic images of the plurality of vessels in the coronary vasculature under a second acquisition condition, wherein the first acquisition condition is a different acquisition condition than the second acquisition condition, the different acquisition condition comprising at least one of a different condition of the patient or a different condition of contrast agent dynamics, and wherein each of the diagnostic images of the first time series of diagnostic images and each of the diagnostic images of the second time series of diagnostic images, respectively, represents a visualization of the contrast agent dynamics for a particular point in time, compute, for the first time series of diagnostic images, a first time series of vessel map feature values of a first dynamic vessel map representing the plurality of vessels under the first acquisition condition, wherein the first time series of vessel map feature values are indicative of evolution of the contrast agent through the coronary vasculature over time under the first acquisition condition, compute, for the second time series of diagnostic images, a second time series of vessel map feature values of a second dynamic vessel map representing the plurality of vessels under the second acquisition condition, wherein the second time series of vessel map feature values are indicative of evolution of the contrast agent through the coronary vasculature over time under the second acquisition condition, and compare the first time series of vessel map feature values under the first acquisition condition and the second time series of vessel map feature values under the second acquisition condition to derive at least one global hemodynamic parameter.

2. The apparatus according to claim 1, wherein the first time series of diagnostic images and the second time series of diagnostic images are obtained using X-ray angiography.

3. The apparatus according to claim 1, wherein:
the first dynamic vessel map represents an inflow of the contrast agent into the plurality of vessels as a function of time under resting conditions; and
the second dynamic vessel map represents an inflow of the contrast agent into the plurality of vessels as a function of time under hyperemic conditions.

4. The apparatus according to claim 1, wherein:
the first dynamic vessel map represents an inflow of the contrast agent into the plurality of vessels as a function of time; and
the second dynamic vessel map represents an outflow of the contrast agent out of the plurality of vessels as a function of time.

5. The apparatus according to claim 1, wherein:
the first time series of vessel map feature values comprises a first plurality of values indicative of an area occupied by the plurality of vessels in each diagnostic image of the first time series of diagnostic images as a function of time; and
the second time series of vessel map feature values comprises a second plurality of values indicative of an area occupied by the plurality of vessels in each diagnostic image of the second time series of diagnostic images as a function of time.

6. The apparatus according to claim 5, wherein to compare the first time series of vessel map feature values and the second time series of vessel map feature values, the processor is further configured to:
determine a first slope value for the first plurality of values indicative of the area occupied by the plurality of vessels as function of time,
determine a second slope value for the second plurality of values indicative of the area occupied by the plurality of vessels as function of time, and
compare the first slope value and the second slope value to derive the at least one global hemodynamic parameter.

7. The apparatus according to claim 1, wherein the processor is further configured to:
derive the at least one global hemodynamic parameter based on the comparison of the first time series of vessel map feature values and the second time series of vessel map feature values and a ground truth for the at least one global hemodynamic parameter.

8. The apparatus according to claim 1, wherein the processor is further configured to:
receive first intravascular measurement data comprising a first pressure value acquired under resting conditions at a proximal measurement position inside a vessel of interest of the plurality of vessels,
receive second intravascular measurement data comprising a first pressure value acquired under hyperemic conditions at the proximal measurement position inside the vessel of interest,
determine a deviation between the first pressure value acquired under resting conditions and the first pressure value acquired under hyperemic conditions,
compare the deviation to a predetermined threshold, and
if the deviation is larger than the predetermined threshold, output a corresponding indication.

9. The apparatus according to claim 8, wherein:
the first intravascular measurement data further comprises a second pressure value acquired under resting conditions at a distal measurement position inside the vessel of interest; and
the second intravascular measurement data further comprises a second pressure value acquired under hyperemic conditions at the distal measurement position inside the vessel of interest;
the processor is further configured to:
determine a value indicative of a hydrostatic pressure difference between the proximal measurement position and the distal measurement position inside the vessel of interest, and
calculate at least one local hemodynamic parameter based on the first pressure value of the first intravascular measurement data, the second pressure value of the first intravascular measurement data, the first pressure value of the second intravascular measurement data, the second pressure value of the second intravascular measurement data, and the value indicative of the hydrostatic pressure difference.

10. The apparatus according to claim 9, wherein the value indicative of the hydrostatic pressure difference comprises a height difference between the proximal measurement position and the distal measurement position.

11. The apparatus according to claim 9, wherein the processor is configured to determine the value indicative of the hydrostatic pressure difference based on at least one diagnostic image obtained from at least one of the first time series of diagnostic images and the second time series of diagnostic images.

12. The apparatus according to claim 1, wherein at least one of:
    the second time series of diagnostic images is acquired with a hyperemic condition of the patient and the first time series of diagnostic images is acquired with the at least one different acquisition condition of a resting condition of the patient, or
    the second time series of diagnostic images is acquired with a contrast agent outflow condition and the first time series of diagnostic images is acquired with the at least one different acquisition condition of a contrast agent inflow condition.

13. A method for assessing a coronary vasculature, the method comprising:
    receiving a first time series of diagnostic images of a plurality of vessels in the coronary vasculature under a first acquisition condition;
    receiving a second time series of diagnostic images of the plurality of vessels in the coronary vasculature under a second acquisition condition,
    wherein the first acquisition condition is a different acquisition condition than the second acquisition condition, the different acquisition condition comprising at least one of a different condition of the patient or a different condition of contrast agent dynamics, and
    wherein each of the diagnostic images of the first time series of diagnostic images and each of the diagnostic images of the second time series of diagnostic images, respectively, represents a visualization of the contrast agent dynamics for a particular point in time;
    computing, for the first time series of diagnostic images, a first time series of vessel map feature values of a first dynamic vessel map representing the plurality of vessels under the first acquisition condition, wherein the first time series of vessel map feature values are indicative of evolution of the contrast agent through the coronary vasculature over time under the first acquisition condition;
    computing, for the second time series of diagnostic images, a second time series of vessel map feature values of a second dynamic vessel map representing the plurality of vessels under the second acquisition condition, wherein the second time series of vessel map feature values are indicative of evolution of the contrast agent through the coronary vasculature over time under the second acquisition condition;
    comparing the first time series of vessel map feature values under the first acquisition condition and the second time series of vessel map feature values under the second acquisition condition; and
    deriving, based on the comparing, at least one global hemodynamic parameter.

14. The method according to claim 13, further comprising:
    receiving first intravascular measurement data comprising a first pressure value acquired under resting conditions at a proximal measurement position inside a vessel of interest of the plurality of vessels and a second pressure value acquired under resting conditions at a distal measurement position inside the vessel of interest;
    receiving second intravascular measurement data comprising a first pressure value acquired under hyperemic conditions at the proximal measurement position inside the vessel of interest and a second pressure value acquired under hyperemic conditions at the distal measurement position inside the vessel of interest;
    determining, based on at least one diagnostic image obtained from at least one of the first time series of diagnostic images and the second time series of diagnostic images, a value indicative of a hydrostatic pressure difference between the proximal measurement position and the distal measurement position inside the vessel of interest; and
    calculating, based on the first and second pressure value of the first intravascular measurement data, the first and second pressure value of the second intravascular measurement data and the value indicative of the hydrostatic pressure difference, at least one local hemodynamic parameter.

15. The method according to claim 13, wherein at least one of:
    the second time series of diagnostic images is acquired with a hyperemic condition of the patient and the first time series of diagnostic images is acquired with the at least one different acquisition condition of a resting condition of the patient, or
    the second time series of diagnostic images is acquired with a contrast agent outflow condition and the first time series of diagnostic images is acquired with the at least one different acquisition condition of a contrast agent inflow condition.

16. The method according to claim 13, wherein comparing the first time series of vessel map feature values and the second time series of vessel map feature values comprises:
    determining a first slope value for the first plurality of values indicative of the area occupied by the plurality of vessels as function of time;
    determining a second slope value for the second plurality of values indicative of the area occupied by the plurality of vessels as function of time; and
    comparing the first slope value and the second slope value to derive the at least one global hemodynamic parameter.

17. A non-transitory computer-readable storage medium having stored a computer program comprising instructions, which, when executed by a processor, cause the processor to:
    receive a first time series of diagnostic images of a plurality of vessels in the coronary vasculature under a first acquisition condition,
    receive a second time series of diagnostic images of the plurality of vessels in the coronary vasculature under a second acquisition condition,
    wherein the first acquisition condition is a different acquisition condition than the second acquisition condition, the different acquisition condition comprising at least one of a different condition of the patient or a different condition of contrast agent dynamics, and
    wherein each of the diagnostic images of the first time series of diagnostic images and each of the diagnostic images of the second time series of diagnostic images, respectively, represents a visualization of the contrast agent dynamics for a particular point in time;
    compute, for the first time series of diagnostic images, a first time series of vessel map feature values of a first dynamic vessel map representing the plurality of vessels under the first acquisition condition, wherein the first time series of vessel map feature values are indicative of evolution of the contrast agent through the coronary vasculature over time under the first acquisition condition;

compute, for the second time series of diagnostic images, a second time series of vessel map feature values of a second dynamic vessel map representing the plurality of vessels under the second acquisition condition, wherein the second time series of vessel map feature values are indicative of evolution of the contrast agent through the coronary vasculature over time under the second acquisition condition; and compare the first time series of vessel map feature values under the first acquisition condition and the second time series of vessel map feature values under the second acquisition condition to derive at least one global hemodynamic parameter.

18. The non-transitory computer-readable storage medium according to claim 17, wherein at least one of:

the second time series of diagnostic images is acquired with a hyperemic condition of the patient and the first time series of diagnostic images is acquired with the at least one different acquisition condition of a resting condition of the patient, or the second time series of diagnostic images is acquired with a contrast agent outflow condition and the first time series of diagnostic images is acquired with the at least one different acquisition condition of a contrast agent inflow condition.

19. The non-transitory computer-readable storage medium according to claim 17, wherein, to compare the first time series of vessel map feature values and the second time series of vessel map feature values, the instructions, when executed by the processor, further cause the processor to:

determine a first slope value for the first plurality of values indicative of the area occupied by the plurality of vessels as function of time;

determine a second slope value for the second plurality of values indicative of the area occupied by the plurality of vessels as function of time; and compare the first slope value and the second slope value to derive the at least one global hemodynamic parameter.

20. The non-transitory computer-readable storage medium according to claim 17, the instructions, when executed by the processor, further cause the processor to:

receive first intravascular measurement data comprising a first pressure value acquired under resting conditions at a proximal measurement position inside a vessel of interest of the plurality of vessels and a second pressure value acquired under resting conditions at a distal measurement position inside the vessel of interest;

receive second intravascular measurement data comprising a first pressure value acquired under hyperemic conditions at the proximal measurement position inside the vessel of interest and a second pressure value acquired under hyperemic conditions at the distal measurement position inside the vessel of interest;

determine, based on at least one diagnostic image obtained from at least one of the first time series of diagnostic images and the second time series of diagnostic images, a value indicative of a hydrostatic pressure difference between the proximal measurement position and the distal measurement position inside the vessel of interest; and calculate, based on the first and second pressure value of the first intravascular measurement data, the first and second pressure value of the second intravascular measurement data and the value indicative of the hydrostatic pressure difference, at least one local hemodynamic parameter.

\* \* \* \* \*